(12) United States Patent
Mathivet

(10) Patent No.: US 8,404,821 B2
(45) Date of Patent: Mar. 26, 2013

(54) PRODUCTION OF ORGANIC SOLVENT SOLUTIONS OF RARE-EARTH ORGANOPHOSPHATES

(75) Inventor: Thomas Mathivet, Marans (FR)

(73) Assignee: Rhodia Operations, Aubervilliers (FR)

( * ) Notice: Subject to any disclaimer, the term of this patent is extended or adjusted under 35 U.S.C. 154(b) by 406 days.

(21) Appl. No.: 12/671,323

(22) PCT Filed: Jul. 8, 2008

(86) PCT No.: PCT/EP2008/058849
§ 371 (c)(1),
(2), (4) Date: Jun. 17, 2010

(87) PCT Pub. No.: WO2009/019100
PCT Pub. Date: Feb. 12, 2009

(65) Prior Publication Data
US 2010/0280264 A1 Nov. 4, 2010

(30) Foreign Application Priority Data

Aug. 8, 2007 (FR) ...................... 07 05766

(51) Int. Cl.
*C07F 5/00* (2006.01)
*C07F 9/02* (2006.01)

(52) U.S. Cl. ............................................ 534/15; 556/24
(58) Field of Classification Search .................... 556/24; 534/15
See application file for complete search history.

(56) References Cited

U.S. PATENT DOCUMENTS 3,702,233 A * 11/1972 Gump et al. ................. 423/21.1
6,767,927 B1 7/2004 Yunlu et al.

FOREIGN PATENT DOCUMENTS

EP 0924214 A2 6/1999
WO WO 00/64910 A1 11/2000

* cited by examiner

*Primary Examiner* — Porfirio Nazario Gonzalez
(74) *Attorney, Agent, or Firm* — SNR Denton US LLP

(57) ABSTRACT

Solutions of rare-earth organophosphates in an organic solvent are prepared by reacting, in such solvent, a rare-earth compound selected from among the rare-earth oxides, hydroxides, carbonates and hydroxycarbonates with an organophosphorus acid and in the presence of a reaction promoter selected from among water, nitric, hydrochloric, acetic, formic and propionic acids and the rare-earth salts of these acids; utilizing a reaction promoter simplifies the method, reduces the reaction time and provides a solution in which the residual solids content may be low.

11 Claims, No Drawings

PRODUCTION OF ORGANIC SOLVENT SOLUTIONS OF RARE-EARTH ORGANOPHOSPHATES

CROSS-REFERENCE TO ALL PRIOR APPLICATIONS

This application is a national phase of PCT/EP 2008/058849, filed July 8, 2008 and designating the United States (published in the French language on Feb. 12, 2009, as WO 2009/019100 A1; the title and abstract were also published in English), and claims priority of FR 0705766, filed Aug. 8, 2007, each hereby expressly incorporated by reference in its entirety and each assigned to the assignee hereof.

The present invention relates to a method for preparing a solution of a rare-earth organophosphate in an organic solvent.

Solutions of rare-earth organophosphates are used in particular as a starting material for the preparation of catalysts for diene polymerization.

The preparation of a solution of a rare-earth organophosphate through the attack of an inorganic rare-earth salt is generally difficult. This is because it requires either a large excess of organophosphoric acid in order to completely dissolve the inorganic rare-earth salt, creating acid residues in the product, the presence of which is not desirable for use, or very long reaction times which are incompatible with industrial use. Moreover, the resulting solution is generally of a high viscosity (>15 000 cPs), which makes it virtually impossible to carry out any operation to filter residual solid present in the product.

It is therefore important to have methods which make it possible to obtain, under industrial conditions, solutions with a low content of inorganic rare-earth salts in solid form and also with an acceptable residual acidity.

The object of the invention is therefore to provide such a method.

To this end, the method of the invention for preparing a solution of a rare-earth organophosphate in an organic solvent is of the type in which a rare-earth compound chosen from rare-earth oxides, hydroxides, carbonates and hydroxycarbonates is reacted with an organophosphorus acid and in the presence of said solvent, and is characterized in that the reaction is carried out in the presence of a promoter chosen from water, nitric acid, hydrochloric acid, acetic acid, formic acid and propionic acid and the rare-earth salts of these acids.

The use of a promoter according to the invention makes it possible in particular to simplify the method, to reduce the reaction time and to obtain a solution of which the residual-solid content may be low.

Other characteristics, details and advantages of the invention will become even more completely apparent on reading the description which follows, and also various concrete but nonlimiting examples intended to illustrate it.

The term "rare-earth" is intended to mean the elements of the group constituted of yttrium and the elements of the periodic table having an atomic number between 57 and 71, limits included.

The method of the invention applies most particularly to the preparation of an organophosphate of a rare-earth element chosen from neodymium, lanthanum, praseodymium, samarium and cerium.

The method of the invention involves reacting a rare-earth compound with an organophosphorus acid.

As rare-earth compounds, use is made of those which were mentioned above. Among these, oxides are preferably used.

The organophosphorus acid may be more particularly chosen from phosphoric acid monoesters or diesters, phosphonic acids and phosphinic acids.

The phosphoric acid monoesters or diesters may correspond to the respective formulae $(RO)PO(OH)_2$ and $(RO)(RTO)PO(OH)$ in which R and R', which may be identical or different, represent alkyl or aryl radicals.

By way of example, R and R' may be n-butyl, isobutyl, pentyl, amyl, isopentyl, 2,2-dimethylhexyl, 2-ethylhexyl, 1-ethylhexyl, octyl, nonyl, decyl, 2,2-dimethyloctyl, tolyl or nonaphenyl radicals.

The organophosphorus acid may also be chosen from phosphonic acids of general formulae $(RO)R'P(O)(OH)$ and $RP(O)(OH)_2$ in which R and R', which may be identical or different, represent alkyl or aryl radicals. By way of example, R and R' may be n-butyl, isobutyl, pentyl, amyl, isopentyl, 2,2-dimethylhexyl, 2-ethylhexyl, 1-ethylhexyl, octyl, nonyl, decyl, 2,2-dimethyloctyl, tolyl or nonaphenyl radicals.

The organophosphorus acid may also be chosen from the phosphinic acids of general formulae $R(RT)P(O)OH$ and $R(H)P(O)OH$ in which R and R', which may be identical or different, represent alkyl or aryl radicals. By way of example R and R' may be n-butyl, isobutyl, pentyl, amyl, isopentyl, 2,2-dimethylhexyl, 2-ethylhexyl, 1-ethylhexyl, octyl, nonyl, decyl, 2,2-dimethyloctyl, tolyl or nonaphenyl radicals.

Mixtures of the organophosphorus acids described above may of course be used.

The essential characteristic of the invention is that the reaction between the rare-earth compound and the organophosphorus acid is carried out in the presence of a promoter of the type given above.

The reaction is generally carried out by mixing the rare-earth compound, the organophosphorus acid and the promoter in the organic solvent.

The organic solvent used is generally a hydrocarbon-based solvent, more particularly an aliphatic, cycloaliphatic or even an aromatic solvent.

This solvent may be chosen from the group comprising hexane, cyclohexane, methylcyclohexane, heptane, methylpentane, methylcyclopentane, pentane, 3-methylpentane, 2-methylpentane, 2,3-dimethylpentane and their isomers, toluene and xylenes, and mixtures thereof. Hexane, cyclohexane, and methylcyclohexane, and isomers thereof and mixtures thereof are preferred.

The commercially available hydrocarbon-based solvents are the Exxsol® hexanes provided by Exxon, the Exxsol® heptane provided by Exxon, the Isopar®, Isopar-M® and Isopar-L® provided by Exxon, the Solvent 140® provided by Exxon, the Mineral Spirits 66® provided by Philips, the cyclohexane provided by BASF and the methylcyclohexane provided by Total Fluides.

The amounts of promoter to be used will be specified below. It will be noted that, in general, the minimum amount is that starting from which the promoter can play a role, i.e. starting from which the yield from the reaction is acceptable. This yield is acceptable when the reaction medium no longer displays any turbidity at the end of the reaction. This amount can therefore be readily determined by those skilled in the art. The maximum amount is not generally critical and can be fixed according to the industrial constraints. The amounts which are given below are done so only by way of illustrative examples and should therefore be understood to lie between these minimum and maximum amounts.

When the promoter is water, an amount of water is used which, expressed by the water/rare-earth molar ratio, is generally between approximately 1 and approximately 500, more particularly between 1 and 300, and even more particularly between 5 and 100. According to one preferred embodiment, this ratio is at least 25, more particularly at least 50 and even more particularly at least 90, it being possible for the upper limits of the values given above to also apply to this embodiment.

When the promoter is an acid, an amount of acid is used which, expressed by the acid/rare-earth molar ratio, is generally between approximately 0.005 and approximately 0.2, or particularly between 0.005 and 0.1, and even more particularly between 0.005 and 0.06.

It may be noted that the acid can be used pure or as a concentrated or dilute solution.

As indicated above, the promoter may be a rare-earth nitrate, chloride, acetate, formate or propionate. In this case, the amount of salt, expressed by the salt/rare-earth molar ratio, is generally between approximately 0.005 and approximately 0.2, more particularly between 0.005 and 0.1.

The reaction of the rare-earth compound with the organophosphorus acid in the presence of the promoter is generally carried out at a temperature of at least 60° C., more particularly between 80° C. and 100° C. Temperatures above 100° C. can nevertheless be envisioned.

The duration of this attack can vary to a large extent, for example between 1 and 6 hours, and in practice it may be between 1 and 2 hours.

Preferably, the reaction is carried out under an inert atmosphere, nitrogen for example, in order to prevent the solution being contaminated with oxygen from the air.

At the end of the reaction, a solution of a rare-earth organophosphate is obtained.

The solution may optionally be washed with water in order to remove the acid residues. This washing may be carried out by mixing the organic solution with water, stirring, leaving to separate by settling out, and then separating the aqueous phase from the organic phase.

This solution may also be optionally subjected to a distillation in order to remove the residual water. It is possible, in this way, to obtain a solution of which the water content is at most 500 ppm, more particularly at most 100 ppm. This water content, expressed by the water/rare-earth molar ratio, may be at most 0.2, more particularly at most 0.04.

The residual acidity, expressed by the organophosphorus acid/rare-earth molar ratio, may be at most 0.75, more particularly at most 0.6, and even more particularly at most 0.4.

The yield from the reaction is high insofar as only a very small amount of starting rare-earth compound remains in solution. The solution in fact has a clear appearance. The yield obtained is generally at least 95%, and a yield of 100% may be achieved.

It is possible to adjust the viscosity of the solution obtained by adding thereto a compound chosen from alcohols, carboxylic acids or phosphoric acids. By way of nonlimiting examples, mention may be made of ethanol, ethylene glycol, propylene glycol, dipropylene glycol, acetic acid and propionic acid.

As indicated above, the solutions of rare-earth organophosphate that are derived from the method of the invention may be used for preparing catalysts for the polymerization of dienes such as butadiene and isoprene.

Examples will now be given.

EXAMPLE 1

3.03 g of neodymium oxide containing 72.4% by weight of neodymium, 17.39 g of di(2-ethylhexyl)phosphoric acid (DEHPA), 80 g of methylcyclohexane (MCH) and 25.9 g of water are introduced into a reactor made inert beforehand with argon. The mixture is stirred and brought to 95° C. until complete disappearance of the solid, i.e., in this case, 1 h. The mixture is cooled and separated by settling out. 22.5 g of water are thus removed from the mixture. The water/MCH azeotrope is subsequently distilled with a Dean Stark apparatus. 84 g of a solution of neodymium di(2-ethylhexyl)phosphate in MCH are thus obtained.

This solution is characterized by a clear appearance, a content of neodymium in solution of 2.65%, a residual free acidity expressed as percentage by weight of DEHPA of 2.2%, and a water content of 382 ppm. In this case, the molar ratios are the following: DEHPA/Nd=0.37 and water/Nd=0.11. The attack yield is 100%.

EXAMPLE 2

3.03 g of neodymium oxide containing 72.4% by weight of neodymium, 17.39 g of di(2-ethylhexyl)phosphoric acid (DEHPA), 80 g of methylcyclohexane (MCH) and 1.8 ml of nitric acid at 0.5 mol/l are introduced into a reactor made inert beforehand with argon. This amount of nitric acid corresponds to 0.06 molar equivalent of $HNO_3$ relative to the neodymium. The mixture is stirred and brought to 80° C. until the presence of solid can no longer be visually distinguished, i.e., in this case, 3 h. The mixture is cooled. Three washes with 20 g of water are successively carried out in order to remove the residues of nitric acid. Each wash comprises a step of stirring for 30 minutes and then a step of separating by settling out, also for 30 minutes, except for the final separating by settling out, which lasts 12 h. 18 g, 18 g and then 23 g of water are thus successively recovered. The water/MCH azeotrope is subsequently distilled with a Dean Stark apparatus. 100 g of a solution of neodymium di(2-ethylhexyl)phosphate in MCH are thus obtained.

This solution is characterized by a clear appearance, a content of neodymium in solution of 2.15%, a residual free acidity expressed as percentage by weight of DEHPA of 3.0%, and a water content of 72 ppm. In this case, the molar ratios are the following: DEHPA/Nd=0.62 and water/Nd=0.03. The attack yield is 98%.

EXAMPLE 3

3.03 g of neodymium oxide containing 72.4% by weight of neodymium, 17.39 g of di(2-ethylhexyl)phosphoric acid (DEHPA), 80 g of methylcyclohexane (MCH) and 0.9 ml of hydrochloric acid at 1 mol/l are introduced into a reactor made inert beforehand with argon. This amount of hydrochloric acid corresponds to 0.06 molar equivalent of HCl relative to the neodymium. The mixture is stirred and brought to 80° C. for 3 h. The mixture is cooled. Three washes with 20 g of water are successively carried out in order to remove the residues of hydrochloric acid. Each wash comprises a step of stirring for 30 minutes and then a step of separating by settling out, also for 30 minutes, except for the final separating by settling out, which lasts 12 h. The water/MCH azeotrope is subsequently distilled with a Dean Stark apparatus. A clear solution of neodymium di(2-ethylhexyl)phosphate in MCH is thus obtained.

This solution is characterized by a clear appearance, a content of neodymium in solution of 2.25%, a residual free acidity expressed as percentage by weight of DEHPA of 2.85%, and a water content of 249 ppm. In this case, the molar ratios are the following: DEHPA/Nd=0.56 and water/Nd=0.09. The attack yield is 100%.

EXAMPLE 4

2.88 g of neodymium oxide containing 72.4% by weight of neodymium, 0.53 g of an aqueous solution of neodymium nitrate containing 24.4% by weight of neodymium, 17.39 g of di(2-ethylhexyl)phosphoric acid (DEHPA), and 80 g of methylcyclohexane (MCH) are introduced into a reactor made inert beforehand with argon. The mixture is stirred and brought to 80° C. until complete disappearance of the solid, i.e., in this case, 1 h. The mixture is cooled. Three washes with 20 g of water are successively carried out in order to remove the inorganic residues. Each wash comprises a step of stirring for 30 minutes and then a step of separating by settling out, also for 30 minutes, except for the final separating by settling out, which lasts 12 h. The water/MCH azeotrope is subsequently distilled with a Dean Stark apparatus. A clear solution of neodymium di(2-ethylhexyl)phosphate in MCH is thus obtained.

This solution is characterized by a clear appearance, a content of neodymium in solution of 2.1%, a residual free acidity expressed as percentage by weight of DEHPA of 3.2%, and a water content of 369 ppm. In this case, the molar ratios are the following: DEHPA/Nd=0.68 and water/Nd=0.14. The attack yield is 99%.

EXAMPLE 5

2.88 g of neodymium oxide containing 72.4% by weight of neodymium, 0.58 g of an aqueous solution of neodymium chloride containing 22.2% by weight of neodymium, 17.39 g of di(2-ethylhexyl)phosphoric acid (DEHPA) and 80 g of methylcyclohexane (MCH) are introduced into a reactor made inert beforehand with argon. The mixture is stirred and brought to 80° C. for 5 h. The mixture is cooled. Three washes with 20 g of water are successively carried out in order to remove the inorganic residues. Each wash comprises a step of stirring for 30 minutes and then a step of separating by settling out, also for 30 minutes, except for the final separating by settling out, which lasts 12 h. The water/MCH azeotrope is subsequently distilled with a Dean Stark apparatus. A clear solution of neodymium di(2-ethylhexyl)phosphate in MCH is thus obtained.

This solution is characterized by a clear appearance, a content of neodymium in solution of 2.05%, a residual free acidity expressed as percentage by weight of DEHPA of 3.3%, and a water content of 406 ppm. In this case, the molar ratios are the following: DEHPA/Nd=0.72 and water/Nd=0.16. The attack yield is 98%.

EXAMPLE 6

3.03 g of neodymium oxide containing 72.4% by weight of neodymium, 16.15 g of di(2-ethylhexyl)phosphoric acid (DEHPA), 80 g of methylcyclohexane (MCH) and 1.8 ml of nitric acid at 0.5 mol/l are introduced into a reactor made inert beforehand with argon. This amount of nitric acid corresponds to 0.06 molar equivalent of $HNO_3$ relative to the neodymium. The mixture is stirred and brought to 80° C. until the presence of solid can no longer be distinguished visually, i.e., in this case, 3 h. The mixture is cooled. Three washes with 20 g of water are successively carried out in order to remove the inorganic residues. Each wash comprises a step of stirring for 30 minutes and then a step of separating by settling out, also for 30 minutes. 20 g, 19.5 g and then 19.5 g are thus recovered. The water/MCH azeotrope is subsequently distilled with a Dean Stark apparatus. A solution of neodymium di(2-ethylhexyl)phosphate in MCH, with a clear appearance, is thus obtained. It is characterized by a content of neodymium in solution of 2.05%, a residual free acidity expressed as percentage by weight of DEHPA of 1.59%, and a water content of 209 ppm. In this case, the molar ratios are the following: DEHPA/Nd=0.34 and water/Nd=0.08. The attack yield is 95%.

EXAMPLE 7

3.03 g of neodymium oxide containing 72.4% by weight of neodymium, 17.39 g of di(2-ethylhexyl)phosphoric acid (DEHPA), 80 g of methylcyclohexane (MCH) and 0.054 g acetic acid at 99.8% are introduced into a reactor made inert beforehand with argon. This amount of acetic acid corresponds to 0.06 molar equivalent of $CH_3COOH$ relative to the neodymium. The mixture is stirred and brought to 80° C. until the presence of solid can no longer be distinguished visually, i.e., in this case, 1 h. The mixture is cooled. Three washes with 20 g of water are successively carried out in order to remove the inorganic residues. Each wash comprises a step of stirring for 30 minutes and then a step of separating by settling out, also for 30 minutes, except for the final separating by settling out, which is for an overnight period. 16 g, 24.2 g and then 17.1 g are thus recovered. The water/MCH azeotrope is subsequently distilled with a Dean Stark apparatus. A solution of neodymium di(2-ethylhexyl)phosphate in MCH, with a clear appearance, is thus obtained. It is characterized by a content of neodymium in solution of 2.3%, a residual free acidity expressed as percentage by weight of DEHPA of 2.65%, and a water content of 77 ppm. In this case, the molar ratios are the following: DEHPA/Nd=0.51 and water/Nd=0.026. The attack yield is 100%.

The invention claimed is:

1. A method for preparing a solution of a rare-earth organophosphate in an organic solvent, comprising reacting a rare-earth compound selected from the group consisting of oxides, hydroxides, carbonates and hydroxycarbonates of a rare earth metal with an organophosphorus acid and in the presence of said solvent, said reaction being carried out in the presence of a promoter therefor selected from the group consisting of nitric acid, hydrochloric acid, acetic acid, formic acid, propionic acid and the rare-earth salts of said acids.

2. The method as defined by claim 1, said organophosphorus acid being selected from the group consisting of phosphoric acid monoesters, phosphoric acid diesters, phosphonic acids and phosphinic acids.

3. The method as defined by claim 1, said organic solvent comprising an aliphatic or cycloaliphatic solvent.

4. The method as defined by claim 1, said rare-earth organophosphate comprising a rare-earth element selected from the group consisting of neodymium, lanthanum, praseodymium, samarium and cerium.

5. The method as defined by claim 1, wherein said reacting the rare-earth compound with the organophosphorus acid is carried out at a temperature of at least 60° C.

6. The method as defined by claim 1, said rare-earth compound comprising a rare-earth oxide.

7. The organic solvent solution of a rare-earth organophosphate produced via the method as defined by claim 1.

8. A method for preparing a solution of a rare-earth organophosphate, said method comprising reacting a rare-earth compound selected from the group consisting of rare-earth oxides, hydroxides, carbonates and hydroxycarbonates with an organophosphorus acid in the presence of a solvent, said reaction being carried out in the presence of water as a promoter, wherein the amount of water present is such that the molar ratio of water/rare-earth metal is at least 25.

9. The method of claim 8, wherein the molar ratio of water/rare-earth metal is at least 50.

10. The method of claim 8, wherein the molar ratio of water/rare-earth metal is at least 90.

11. The organic solvent solution of a rare-earth organophosphate produced via the method as defined by claim 8.

* * * * *